(12) United States Patent
Burke

(10) Patent No.: US 8,844,388 B2
(45) Date of Patent: *Sep. 30, 2014

(54) SYSTEM AND METHOD FOR INTERFACING SENSORS TO A STERILE FLOW STREAM

(71) Applicant: EMD Millipore Corporation, Billerica, MA (US)

(72) Inventor: Aaron Burke, Hamilton, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/080,466

(22) Filed: Nov. 14, 2013

(65) Prior Publication Data

US 2014/0073040 A1    Mar. 13, 2014

Related U.S. Application Data

(63) Continuation of application No. 12/079,323, filed on Mar. 26, 2008, now Pat. No. 8,640,560.

(51) Int. Cl.
| | | |
|---|---|---|
| *G01D 21/00* | (2006.01) | |
| *A61L 2/26* | (2006.01) | |
| *G01L 19/06* | (2006.01) | |
| *B01D 63/00* | (2006.01) | |
| *C12M 1/12* | (2006.01) | |

(52) U.S. Cl.
CPC C12M 37/02 (2013.01); A61L 2/26 (2013.01); G01L 19/0645 (2013.01); B01D 63/00 (2013.01)
USPC .......................................................... 73/866.5

(58) Field of Classification Search
None
See application file for complete search history.

(56) References Cited

U.S. PATENT DOCUMENTS

| | | |
|---|---|---|
| 3,818,765 A | 6/1974 | Eriksen |
| 4,141,252 A | 2/1979 | Lodge |
| 4,415,858 A | 11/1983 | Hale |
| 4,463,593 A | 8/1984 | Parker |
| 4,695,551 A | 9/1987 | Samhaber et al. |
| 4,700,560 A | 10/1987 | Hoffa et al. |
| 4,786,474 A | 11/1988 | Cooper |
| 5,178,267 A | 1/1993 | Grabenkort et al. |
| 5,976,085 A | 11/1999 | Kimball et al. |

(Continued)

FOREIGN PATENT DOCUMENTS

| | | |
|---|---|---|
| DE | 10345299 B3 | 7/2005 |
| EP | 1199556 A1 | 4/2002 |

(Continued)

OTHER PUBLICATIONS

International Search Report/Written Opinion mailed May 13, 2009 in corresponding PCT application No. PCT/US 09/01616.

(Continued)

*Primary Examiner* — Robert R Raevis
(74) *Attorney, Agent, or Firm* — Nields, Lemack & Frame, LLC

(57) ABSTRACT

A system and method for interfacing non-sterile sensors to a sterile flow stream is disclosed. Typically, sensors cannot be sterilized in the same manner as other components of the flow stream. This results in complex processes to incorporate a sterilized sensor into a sterilized flow stream. By introducing a separation membrane, the desired sensor can be interfaced to the sterile flow stream. By doing so, the sensor need not be sterile, only sufficiently clean. The membrane separates the sterile environment within the flow stream from the sensor, while still permitting the sensor to function.

21 Claims, 5 Drawing Sheets

(56) References Cited

U.S. PATENT DOCUMENTS

| | | |
|---|---|---|
| 6,883,377 B2 | 4/2005 | Doubrovsky |
| 6,926,814 B2 | 8/2005 | Koenemann et al. |
| 7,470,060 B1 | 12/2008 | Hoben et al. |
| 7,540,197 B2 | 6/2009 | Wavering et al. |
| 7,918,134 B2 | 4/2011 | Hedtke et al. |
| 8,297,128 B2 | 10/2012 | Delbos et al. |
| 8,485,044 B2 | 7/2013 | Delbos et al. |
| 8,640,560 B2 | 2/2014 | Burke |
| 2002/0189363 A1 | 12/2002 | Doubrovsky |
| 2003/0017078 A1 | 1/2003 | Trapp et al. |
| 2007/0185472 A1 | 8/2007 | Baumfalk et al. |
| 2008/0141780 A1 | 6/2008 | Wavering et al. |
| 2008/0247906 A1 | 10/2008 | Heffels et al. |
| 2009/0101213 A1 | 4/2009 | Kielb |
| 2009/0214387 A1 | 8/2009 | Straub et al. |
| 2009/0247989 A1 | 10/2009 | Burke |
| 2009/0260438 A1 | 10/2009 | Hedtke |
| 2009/0293625 A1 | 12/2009 | Sundet et al. |
| 2010/0015656 A1 | 1/2010 | Seitz et al. |
| 2010/0083731 A1 | 4/2010 | Hedtke |
| 2011/0041619 A1 | 2/2011 | Delbos et al. |
| 2013/0003780 A1 | 1/2013 | Delbos et al. |

FOREIGN PATENT DOCUMENTS

| | | |
|---|---|---|
| EP | 2226087 A1 | 9/2010 |
| EP | 2264304 A1 | 12/2010 |
| GB | 1365769 | 9/1974 |
| JP | 2005-524081 A | 8/2005 |
| WO | 03/093780 A1 | 11/2003 |
| WO | 2005/100957 A1 | 10/2005 |
| WO | 2007/131593 A1 | 11/2007 |
| WO | 2008/011876 A2 | 1/2008 |

OTHER PUBLICATIONS

European Communication mailed Sep. 13, 2011 in corresponding European patent application EP 09724042.8.

European Communication dated Jun. 20, 2013 in European patent application No. EP 09725626.7.

Japanese Communication, with English translation, mailed Oct. 23, 2012 in corresponding Japanese Patent Application No. 2011-501788.

French Search Report mailed Oct. 7, 2009 in French patent application No. FR 0951600.

SYSTEM AND METHOD FOR INTERFACING SENSORS TO A STERILE FLOW STREAM

This application is a continuation of U.S. patent application Ser. No. 12/079,323, filed Mar. 26, 2008, the disclosure of which is incorporated herein by reference in its entirety.

BACKGROUND OF THE INVENTION

The production and processing of biocomponents most often requires a sterile environment. To achieve this objective, the systems themselves obviously must be sterilized. Sterilization methods include autoclave, steam-in-place (SIP), gamma irradiation and others. Unfortunately, often, a single sterilization method cannot be used for all components within the system. For example, gamma irradiation is an excellent method of sterilization for certain components, such as disposable bags, tubes, glass, and other similar parts. However, this method is known to be harmful to electronic devices, often destroying the delicate semiconductor structures.

Consequently, it has become necessary to adopt complex procedures to achieve the desired level of system sterilization. It should be noted that sterile, as used in this disclosure, defines a germ free environment. However, sterile does not have to be a complete absence of germs or foreign bodies. Rather, sterile may denote an environment having a predetermined maximum number of germs or foreign bodies. It may also denote an environment with a maximum predetermined size of the germs or foreign bodies found in the environment.

In some cases, these procedures require that the different components be sterilized in the most suitable method available for each. These components are then assembled in a clean room environment. Unfortunately, this adds significant time and cost to the process, especially when considering that many of the components being used are disposable.

United States Patent Publication No. 2007/0185472, assigned to Sartorius, describes a second potential solution to this problem. This application discloses the use of complementary connectors to mate sensors to flow stream components. Displaceable sterile coverings are placed on these complementary connectors. In summary, these coverings ensure that the respective connectors remain sterile. As the connectors are engaged with one another, the coverings slide away, allowing a fluid path between the connectors. In this way, the device attached to the first connector and the device attached to the second connector can be sterilized separately and assembled without the need for a sterile environment.

While this system eliminated the need for a clean room environment, this method still requires separate sterilization procedures for the various system components. A simpler procedure is still necessary.

SUMMARY OF THE INVENTION

The present invention provides a system and method for interfacing non-sterile sensors to a sterile flow stream. As stated above, sensors cannot be sterilized in the same manner as other components of the flow stream. This results in complex processes to incorporate a sensor into a sterilized flow stream.

The present invention connects the desired sensor to the sterile flow stream through the use of a sterile grade membrane. By doing so, the sensor need not be sterile, only sufficiently clean. The membrane serves to separate the sterile environment within the flow stream from the sensor, thereby reducing the time needed to interface a sensor to a sterile flow path and reducing the time and cost of sterilizing the sensor itself.

DETAILED DESCRIPTION OF THE DRAWINGS

There is a requirement to measure a variety of characteristics and parameters within a sterile flow stream. This requirement gives rise to the necessity of adding sensors, which are usually electronic in nature. As stated above, the preferred method of sterilization for electronic components is different from that of the rest of the flow stream. While gamma irradiation is the preferred method of sterilization tubes, bags and other components of the flow stream, this form of sterilization is harmful to electronics.

The present invention utilizes a sterile separation membrane to cover a sensor port in the flow stream. This membrane is preferably permanently affix to the flow stream and can be sterilized with the rest of the flow path components.

Figure 1:
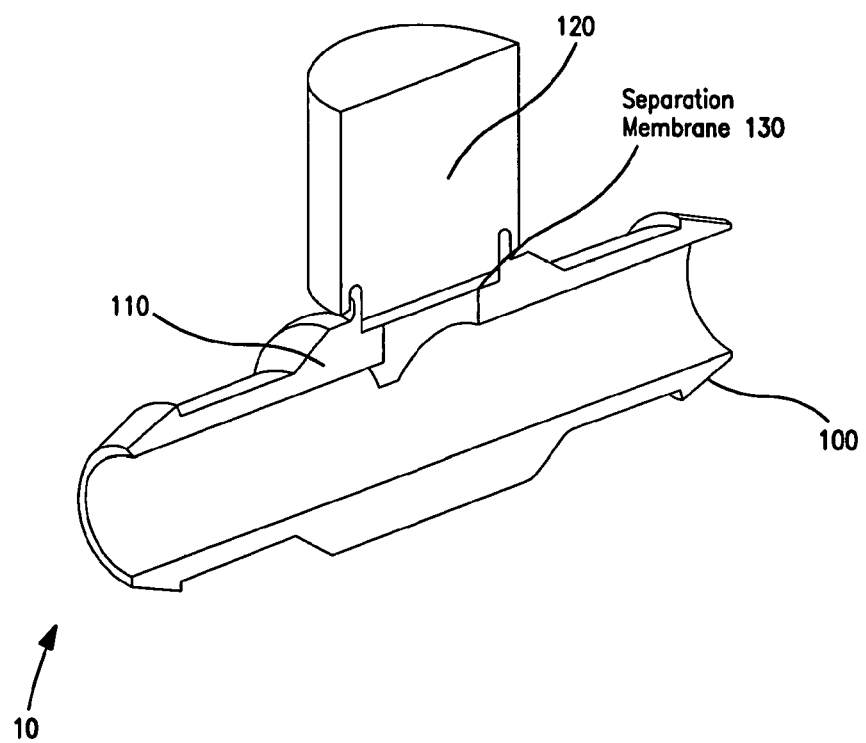
FIG. 1 is a representative illustration of the present invention.

FIG. 1 shows a representative embodiment of the present invention. The tube 100 is part of the sterile flow stream 10. The tube 100 comprises one or more sensor ports 110. The port has a receptacle adapted to accept and hold a sensor device 120 in place. The means used to hold the sensor 120 can be varied. For example, the sensor device 120 can be screwed onto a threaded receptacle. Alternatively, it can be press fit onto a receptacle. In another embodiment, the sensor comprises protrusions that can be laterally slid into corresponding grooves in the receptacle. In another embodiment, it can be held in place with a fastener. In a further embodiment that use of a clamp such as a Tri-Clover clamp or Laddish clamp or band clamp can be used. In another embodiment the sensor can be bonded to the port such as by adhesives or heat sealing or vibration welding or overmolding a retainer around the sensor 120 and port 110 interface to lock them together. These are just illustrations of the various methods that can be used to secure the sensor to the receptacle; it is not intended to be a complete list of all such methods. Other securing means known to those skilled in the art are within the scope of this invention.

The sensor 120, which is not sterile, remains physically separated from the flow stream 10 because of the presence of a separation membrane 130. This membrane ensures that the flow stream remains sterile by prohibiting the passage of foreign bodies through it. This membrane 130 is permanently attached and the inner face of the membrane (that facing the flow path 10) is sterilized with the rest of the flow path 10.

Flow path 10 is pictured in FIG. 1 as a tube. However, the invention is not so limited. The flow path may be comprised of a filter, a bag, or any suitable container. The term flow path is used to denote any component in direct communication with the sterile flow stream. The sensor port may be located anywhere in the flow path, including, but not limited to the entry tube, exit tube, or within the bioreactor bag.

Figure 2:
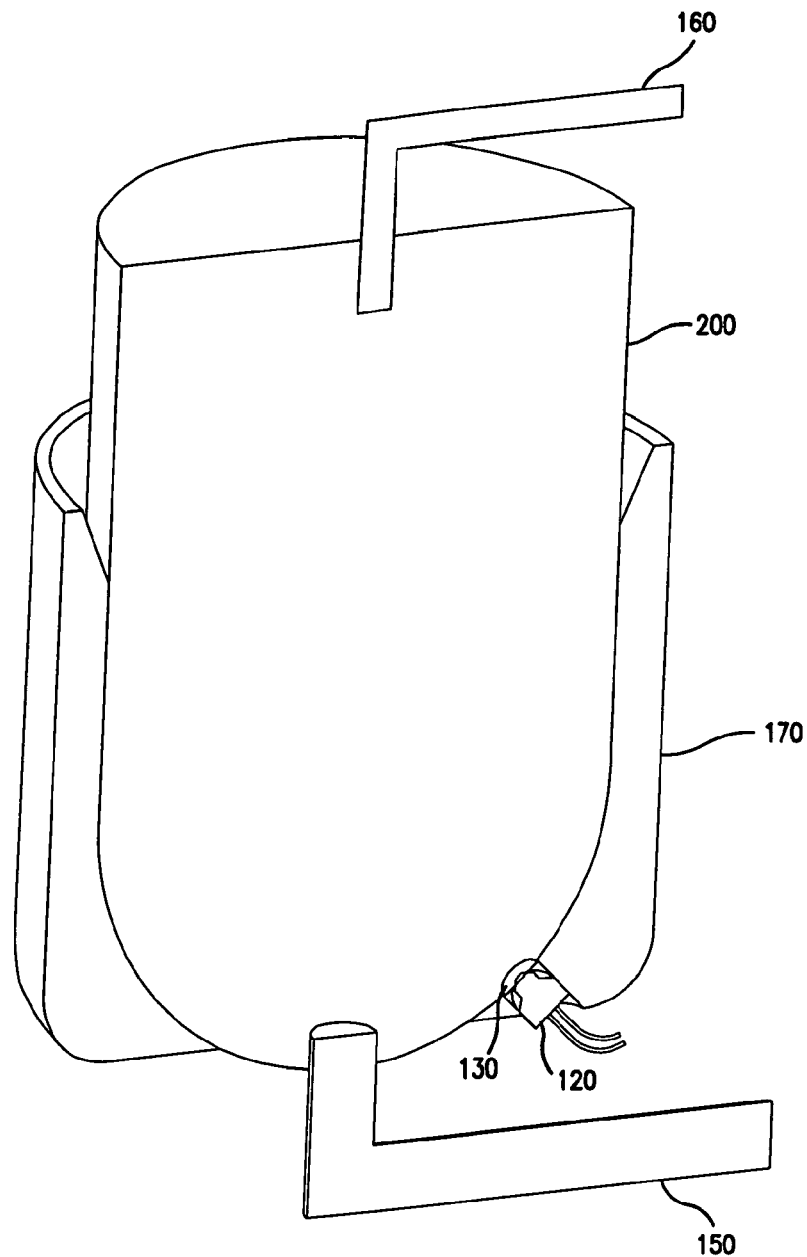
FIG. 2 illustrates a first embodiment of the present invention.
Figure 3:
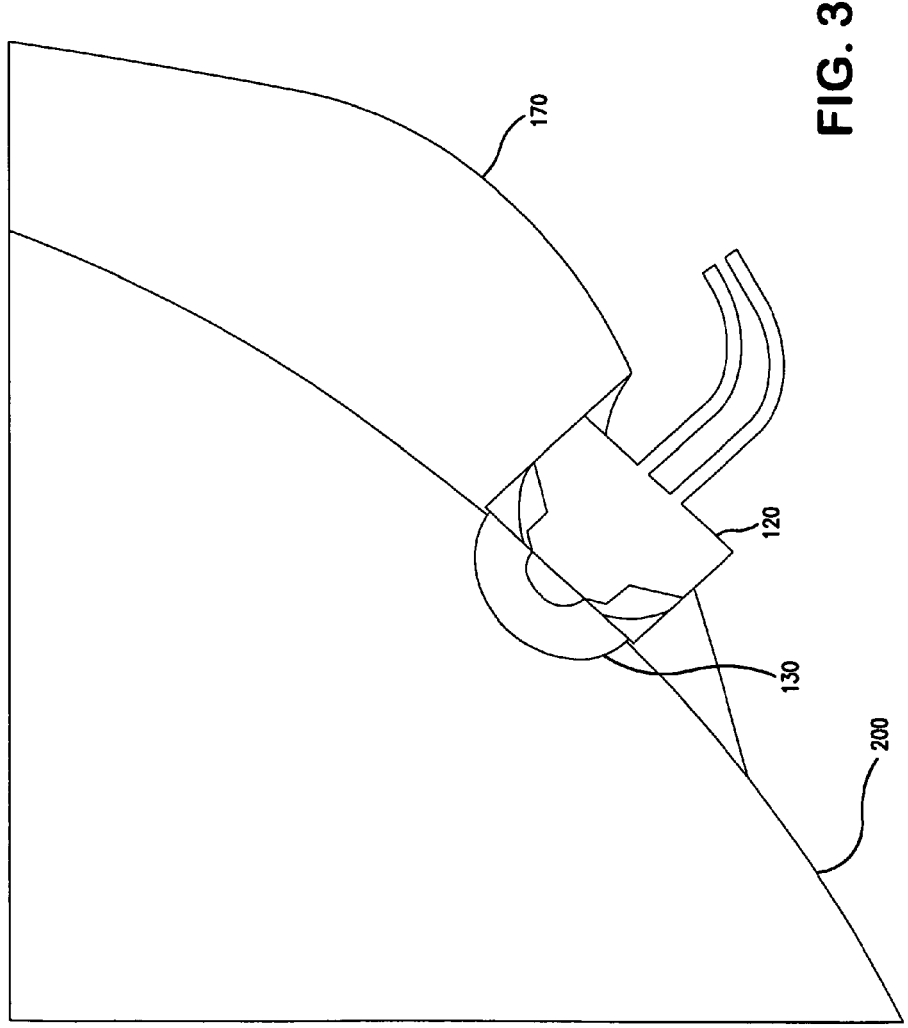
FIG. 3 shows an expanded view of FIG. 2.

For example, FIG. 2 illustrates the use of the present invention with a bioreactor bag 200. Bioreactor bag 200 has an inlet conduit 160 and an outlet conduit 150. In some embodiments, the bioreactor bag is supported by a surrounding structure 170. In this embodiment, the surrounding structure 170 has a passage into which sensor 120 can be placed. As before, sensor 120 is separated from the interior of bioreactor bag 200 by a separation membrane 130. The separation membrane 130 is integrated into the bag so as to sustain a sterile separation during attachment, use and removal of the sensor 120. The separation membrane is attached to the bag, such as by thermal welding or adhesive or other means. The sensor attachment can be accomplished by any means. For example, those of ordinary skill in the art would realize that a alignment sleeve and quarter turn locking mechanism or a tapped hole and threaded sensor body could be used, as well as clamps and the like. These embodiments only suggest means of location or attachment of the sensor to the bioreactor bag and membrane assembly but do not limit the claims of this invention. FIG. 3 shows an expanded view of this embodiment, where like parts share common reference designators.

Alternatively, the receptacle can be incorporated into the plastic bioreactor bag, similar to the scenario shown in FIG. 1.

Figure 4:
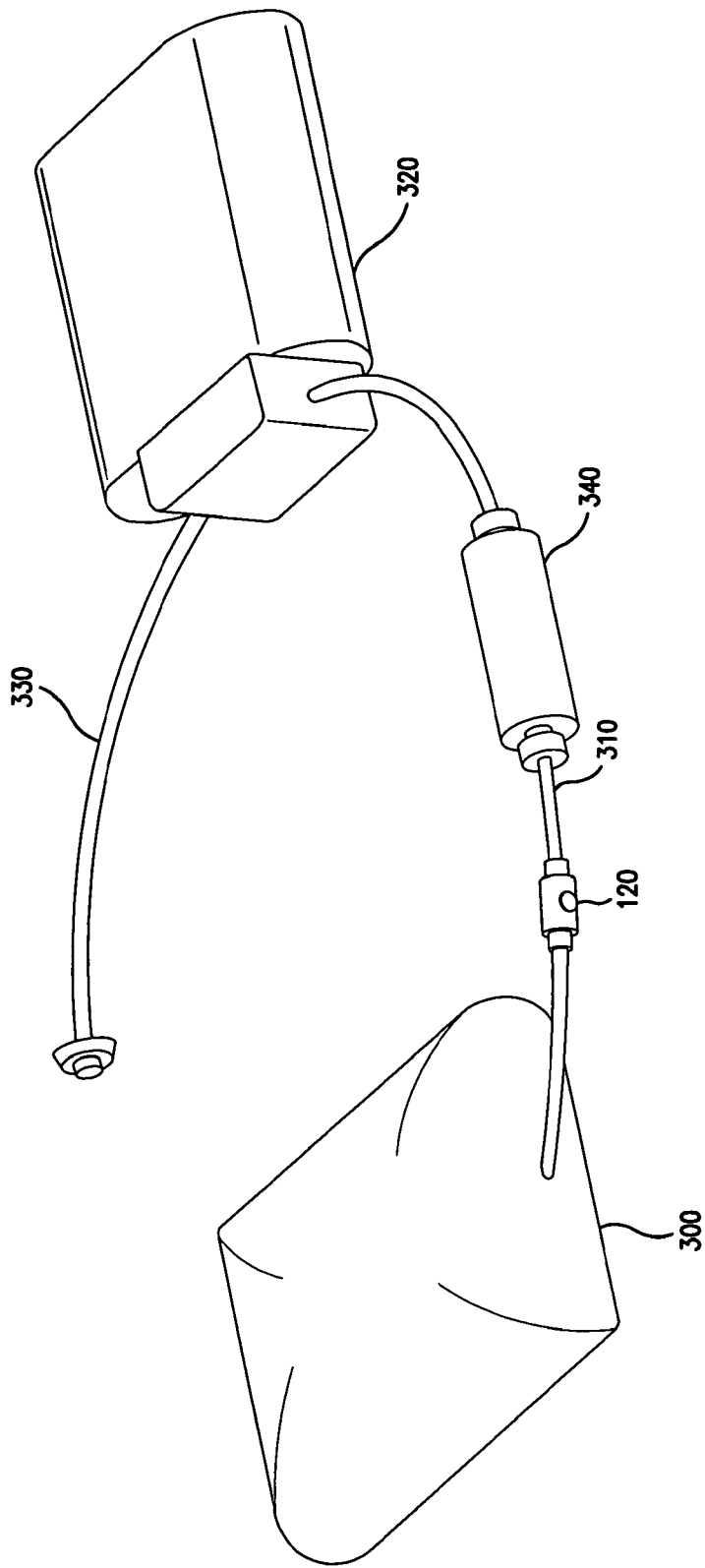
FIG. 4 illustrates a second embodiment of the present invention.
Figure 5:
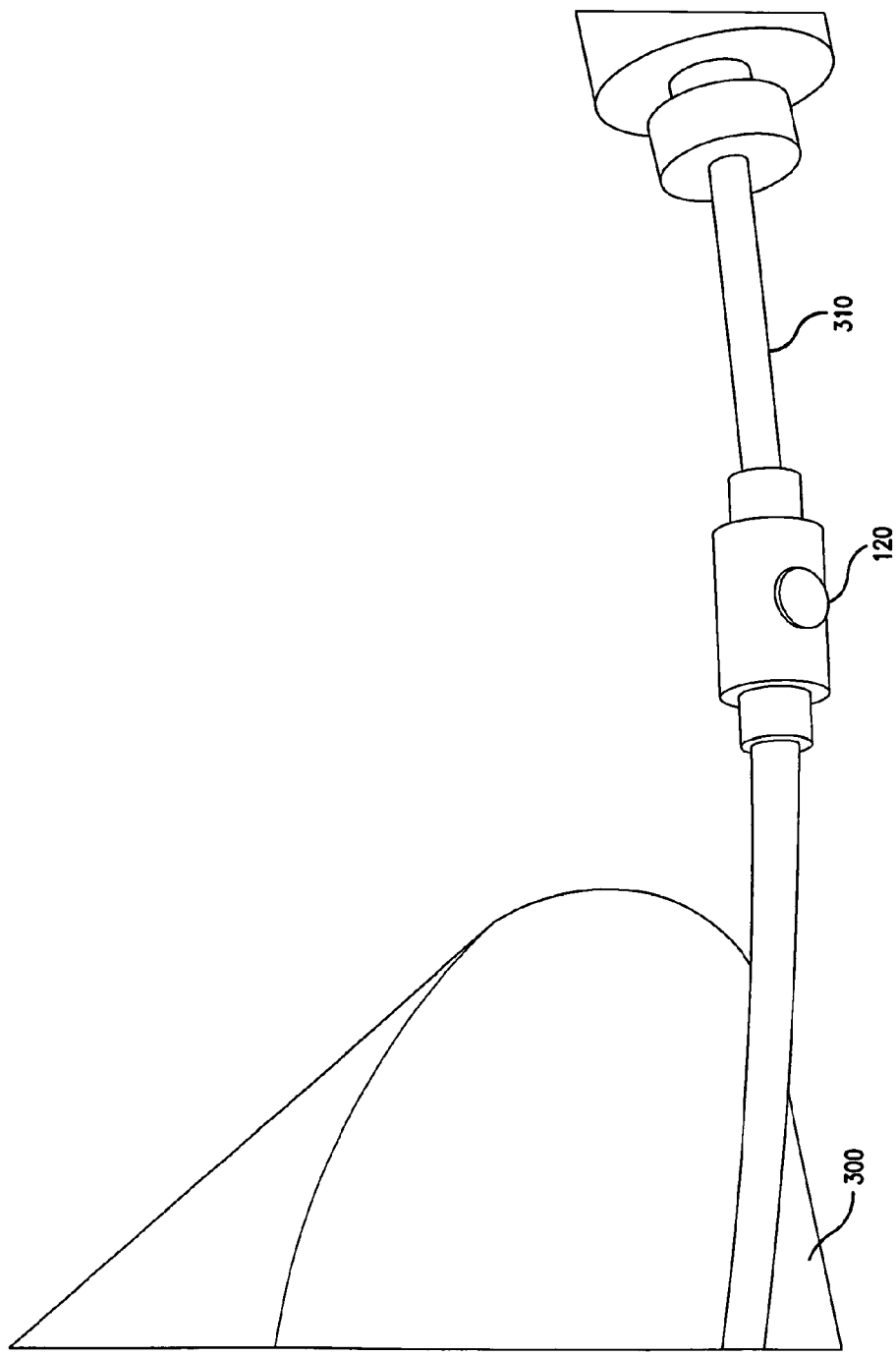
FIG. 5 shows an expanded view of FIG. 4.

FIG. 4 shows a flow path comprising bioreactor bag 300, tube 310, mechanical pump 320 and tube 330. While a sensor port can be incorporated in any of these components, in this embodiment, the sensor 120 is incorporated in the tube 310, which is downstream of filtering element 340. In operation, fluid is moved through tube 330 by mechanical pump 320. It is then pumped out of pump 320 and into tube 310. It then passes through filtering element 340, where it is sterilized. Thus, material exiting filtering element 340 would be considered sterile. At a location downstream of the filtering element 340, a sensor 120 is placed. This sensor can be used to perform any of a variety of function. Thus, by placing a sensor in the tubing 310, the characteristics of the fluid that is eventually deposited in the bioreactor bag 300 can be monitored. FIG. 5 shows an expanded view of FIG. 4, where the sensor 120 is located between the filtering element 340 and the bioreactor bag 300. As stated earlier, the sensor can be inserted anyway in the flow stream. For example, the incoming fluid can be monitored by placing a sensor in tubing 330 or in tubing 320 before filtering element 340. Alternatively, the sterilized fluid can be monitored by placing a sensor on bioreactor bag 300 (as shown in FIG. 2). Additionally, if bioreactor bag 300 has an outlet conduit, a sensor can be located in that conduit as well.

Sensors can be classified in two categories. The first is non-invasive. These types of sensors can perform their required function without invading the sterile environment. One such sensor is a temperature sensor. The second category is invasive sensors. These sensors must be exposed to the flow path in order to perform their required function.

The first category, non-invasive sensors, can easily by accommodated by the present invention. Some parameters, such as temperature and pressure, can be measured simply by being proximate to the flow path. Temperature sensors simply require a sufficiently thermally conductive membrane to perform Mass Flow measurements or temperature measurements of the process material. Similarly, pressure sensors can be employed. The pressure sensor need only be located directly against the membrane to maintain its accuracy. In both of these scenarios, a semi-permeable or impermeable membrane can be utilized. To perform sufficiently accurate pressure measurements, the membrane is made of a sufficiently flexible material such that it deflects under differential pressure and remains continuous and does not break or lose the ability to retain sterile separation. For instance, in one embodiment, a membrane is utilized that is semi-permeable but where the pore size does not become misshapen and therefore compromise the sterile separation. The design of the membrane including the acting flexible surface area and mechanical connection to a pressure sensor face could be done by one skilled in the art.

The second category, invasive sensors can be further categorized as slightly invasive or intrusive. Slightly invasive sensors require exposure to the flow path; however, the particles to which they need to be exposed are very small, allowing them to pass through semi-permeable membranes. Thus, the membrane permits the flow of the necessary smaller particles from the flow path to the sensor, without allowing contaminants from the sensor to enter the flow path. In contrast, intrusive sensors require exposure to the entire flow stream. Thus, in order to be exposed to the flow stream, contaminants from the sensor will necessarily be introduced into the flow path.

Slightly invasive sensors are within the scope of the invention. Slightly invasive sensors include conductivity sensors, dissolved oxygen sensors, dissolved hydrogen sensors and pH sensors. In one embodiment, a sterile-grade membrane is used to cover the receptacle. This membrane permits the passage of small particles, such as hydrogen or oxygen molecules. However, large molecules, such as biological contaminants, cannot pass through the membrane. Thus, this filter permits the passage of necessary materials to the sensor, but does not permit the passage of contaminants back to the flow path. One embodiment comprises a nonsterile pH sensor used with the sterile grade membrane. Fluid and compounds from the sterilized flow stream that are sufficiently small may pass through the membrane and contact the pH electrode. Aqueous salts and other small molecule compounds will pass through the membrane and chemically interact with the pH electrode thereby detecting the pH units of the sterile solution. Any larger molecules, including viruses, complex bacteria and other endotoxins, will not get carried back across the sterile-grade membrane with the salts. The membrane material is chosen to allow efficient passage of certain compounds but block larger more nefarious organisms from passing back into the sterile side. In one embodiment, a 0.22 um Durapore® sterilizing grade membrane (made of PVDF) can be used. As described above, the choice of membrane is an implementation decision, and is based on several factors, including the size of the contaminants that must be kept out of the sterile flowpath, the size of the particles of interest (such as hydrogen or oxygen molecules, salts, etc) and the required rigidity of the membrane. In addition, it is envisioned that the membrane substructure can be chosen to be appropriate for the type of sensor. For instance, asymmetric 0.1 micron Millipore Express® membranes may allow for efficient transfer of small molecule compounds while limiting surface plugging. In addition, a UF filter may be used to allow passage of fluids and salts necessary for the proper operation of a conductivity sensor.

The present invention requires that the separation membrane be an integral part of the flow path, and that the surface of the membrane that faces the flow path is sterilized with the flow path components. This separation membrane covers a port or receptacle that is adapted to receive a sensor. Because of the presence of the separation membrane, this sensor remains separated from the flow stream, and thus cannot introduce contaminants into the stream.

In one embodiment, the separating membrane is chosen from a family of radiation stable materials. It is further contemplated that the attachment of the membrane be performed in such a way that the membrane is not removable and that attachment of the sensor does not break or compromise the integrity of the membrane.

After the flow stream component(s) have been sterilized such as by radiation or the like, the sensor is then attached to the port that contains the membrane.

What is claimed is:

1. A bioreactor system, comprising:
   a bioreactor bag;
   a separation membrane integrated into and permanently affixed to said bioreactor bag, so as to separate an interior of said bioreactor bag from an external environment; and
   a non-sterilized sensor disposed outside of said bioreactor bag proximate to said separation membrane, such that said separation membrane does not permit passage of contaminants present on said sensor into said bioreactor bag.

2. The bioreactor system of claim 1, wherein said separation membrane is thermally welded to said bioreactor bag.

3. The bioreactor system of claim 1, wherein said separation membrane is adhered to said bioreactor bag.

4. The bioreactor system of claim 1, further comprising a supporting structure configured to hold said bioreactor bag, said supporting structure comprising a passage, aligned with said separation membrane, wherein said sensor is disposed in said passage.

5. The bioreactor system of claim 4, wherein a body of said sensor is threaded, such that said sensor body is screwed into said passage.

6. The bioreactor system of claim 4, further comprising a locking mechanism in communication with said passage, said locking mechanism used to hold said sensor in said passage.

7. The bioreactor system of claim 4, wherein said sensor is held in said passage using a clamping mechanism.

8. The bioreactor system of claim 1, wherein said sensor comprises a pH sensor.

9. The bioreactor system of claim 1, wherein said sensor comprises a temperature sensor.

10. The bioreactor system of claim 1, wherein said sensor comprises an oxygen sensor.

11. The bioreactor system of claim 1, wherein said sensor comprises a pressure sensor.

12. The bioreactor system of claim 1, wherein said sensor comprises a conductivity sensor.

13. The bioreactor system of claim 1, wherein said separation membrane is impermeable.

14. The bioreactor system of claim 1, wherein said separation membrane is semi-permeable.

15. A system comprising:
    a bioreactor bag, having an inlet conduit;
    a filtering element, having a downstream side through which filtered material passes, and an unfiltered upstream side;
    a tube in communication with said downstream side of said filtering element and said inlet conduit of said bioreactor bag; and
    a separation membrane, where said separation membrane is disposed in a position such that an unsterilized sensor can monitor a characteristic of said filtered material and said separation membrane does not permit passage of contaminants present on said sensor into said filtered material.

16. The system of claim 15, wherein said separation membrane is integrated into and permanently affixed to said tube.

17. The system of claim 15, wherein said separation membrane is integrated into and permanently affixed to said bioreactor bag, so as to separate an interior of said bioreactor bag from said unsterilized sensor.

18. The system of claim 15, wherein said separation membrane is disposed in an outlet conduit of said bioreactor bag.

19. The system of claim 15, wherein said separation membrane is impermeable.

20. The system of claim 15, wherein said separation membrane is semi-permeable.

21. The system of claim 15, wherein said sensor is selected from the group consisting of a pH sensor, a temperature sensor, an oxygen sensor, a pressure sensor, and a conductivity sensor.

* * * * *